United States Patent [19]

Taylor

[11] Patent Number: 4,939,090
[45] Date of Patent: Jul. 3, 1990

[54] METHOD OF REACTING IMMISCIBLE LIQUIDS WITH A CATALYST-IMPREGNATED MEMBRANE

[75] Inventor: Frank Taylor, Ambler, Pa.

[73] Assignee: United States of America as represented by the Secretary of Agriculture, Washington, D.C.

[21] Appl. No.: 860,360

[22] Filed: May 6, 1986

[51] Int. Cl.$^5$ .................. C12P 7/64; C12N 11/02; C12N 11/08; C12N 9/20
[52] U.S. Cl. .................. 435/134; 435/174; 435/177; 435/180; 435/182; 435/198; 435/288
[58] Field of Search .............. 435/134, 174, 177, 180, 435/182, 198, 288

[56] References Cited

U.S. PATENT DOCUMENTS

| | | | |
|---|---|---|---|
| 4,266,026 | 5/1981 | Breslau | 435/182 X |
| 4,795,704 | 1/1989 | Matson | 435/180 X |

FOREIGN PATENT DOCUMENTS

| | | | |
|---|---|---|---|
| 0210893 | 11/1984 | Japan | 435/134 |
| 1085196 | 4/1986 | Japan | 435/134 |

OTHER PUBLICATIONS

Hoq et al., JAOCS, vol. 62, No. 2, 1985, pp. 1016–1021.
Hoq et al., Agric. Biol. Chem., vol. 49, No. 11, 1985, pp. 3171–3178.

*Primary Examiner*—David M. Naff
*Attorney, Agent, or Firm*—M. Howard Silverstein

[57] ABSTRACT

Reactions involving immiscible liquids are carried out by forcing one immiscible liquid through a catalyst-impregnated membrane. In a preferred embodiment, oil is hydrolyzed by passing the oil on one side of a hydrophilic, microporous membrane impregnated with an enzyme catalyst such as lipase, and passing an aqueous liquid on the other side while forcing oil through the membrane by pressure. Oil flowing through the membrane mixes with the aqueous liquid and resultant immiscible phases are separated. Hydrolysis of the oil into glycerol and fatty acids occurs at catalyst sites in the membrane. The membrane is impregnated with the enzyme catalyst by passing an aqueous solution of the enzyme in contact with the membrane so that the enzyme is adsorbed by the membrane, and removing the aqueous solution after the enzyme is adsorbed.

5 Claims, 1 Drawing Sheet

METHOD OF REACTING IMMISCIBLE LIQUIDS WITH A CATALYST-IMPREGNATED MEMBRANE

FIELD

The present invention relates to reacting two immiscible fluids with one another.

PRIOR ART

It is known in the prior art that immiscible fluids may be reacted with one another at a catalyst-impregnated membrane interface. See M. M. Hoq et al., *J. Am. Oil Chem. Soc.*, 61, p776, 1984; M. M. Hoq et al., *Agric. Biol. Chem.*, 49, p335, 1985; M. M. Hoq et al., *Agric. Biol. Chem.*, 49, p3171, 1985; M. M. Hoq et al., *J. Am. Oil Chem. Soc.*, 62, p1016, 1985. Such a system permits relatively low temperatures and pressures in the reaction zone. In comparison, immiscible reactant liquids such as oil and aqueous solutions ordinarily must be subjected to relatively high temperatures and pressures in order to create an appropriate reaction environment. The use of catalysts involves mild reaction conditions, and the use of a catalyst-impregnated membrane interface readily permits an essentially continuous process.

SUMMARY

The present invention is an improvement of the use of a catalyst-impregnated membrane. Prior to the present invention it was believed that movement of one of the immiscible fluid reactants through the membrane was undesirable, and that such movement would displace catalyst from the membrane. As a result, the pressures on each side of the membrane essentially were equal. In the present invention it was discovered that not only does such movement through the membrane not adversely affect the catalyst, but it results in a system which is easier to control and operate. In addition higher reaction activity is attainable. One of the reactants such as oil need not have to diffuse into the membrane to reach the catalyst, and the fatty acid reaction products formed therefrom need not have to diffuse back through the membrane to the oil side.

Futhermore, by intentionally forcing the reactant such as oil through the membrane, stagnant oil layers which ordinarily may remain in contact with the catalyst, and which make it difficult for unreacted oil to reach the catalyst, are reduced in thickness.

Still further, increasing the pressure drop across the membrane, i.e., pumping the oil more rapidly therethrough, reduces the stagnant, reaction-robbing oil films on the catalyst particles within the membrane.

DETAILED DESCRIPTION

The present invention will be specifically described with regard to hydrolyzing an oil such as melted tallow or olive oil, but it should be understood that the invention is suitable for reacting any two immiscible fluids, including a gas and a liquid, which can be expected to react with one another at a catalyst-impregnated membrane interface.

Figure 1:
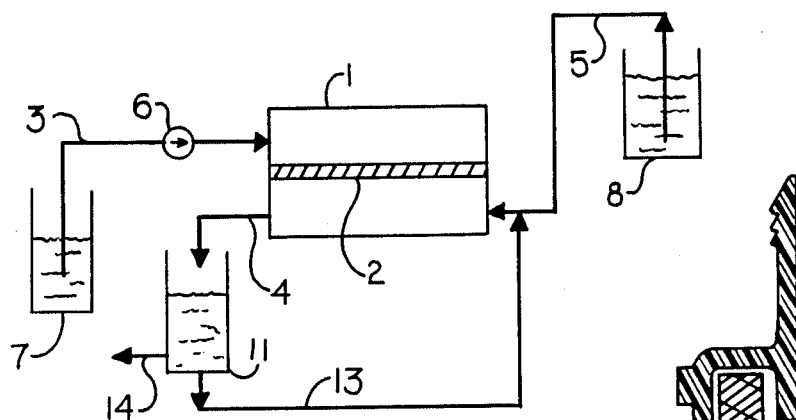
FIG. 1 is a schematic diagram of a flow-through reactor system for hydrolyzing oil.

Referring to FIG. 1, a reaction chamber 1 containing a conventional unloaded membrane 2, is loaded with catalyst by passing a solution of the catalyst into the chamber through conduit 3, either by gravity or by pumping. The solution passes through the membrane and out of the chamber through conduit 4, resulting in the retention or adsorption of catalyst in the membrane. Alternatively, the catalyst may be loaded on the membrane simply by contacting the membrane on either or both sides with the catalyst solution, with minimal or no flow of catalyst solution through the membrane.

After the last of the catalyst solution has passed out of the chamber, the reaction procedure may begin. One reactant such as an oil phase, for example melted tallow at 45°-50° C., is passed into the chamber adjacent one side of the membrane 2 through conduit 3. The other reactant, e.g., an aqueous solution such as a buffer solution, is passed into the chamber by conduit 5 to be adjacent the other side of membrane 2. A pressure drop is maintained across the membrane from the oil side to the aqueous side by conventional means such as peristaltic pump 6 in conduit 3 which conveys oil at elevated pressure into the chamber from an oil reservoir 7, while the aqueous phase may be introduced by gravity from reservoir 8 or by means of a comparatively low pressure pump in supply conduit 5.

The pressure drop intentionally forces oil through the membrane to mix with the aqueous phase on the other side in a coarse mixture. As used in the specification and claims, the phrase "coarse mixture" means that the mixture is not an emulsion, and easily is separated into two phases in a separatory chamber. Hydrolysis of the oil into glycerol and fatty acids occurs at the catalyst sites in the membrane.

The coarse mixture is removed from said other side, i.e., the initially aqueous side, of the chamber through conduit 4 to a separation chamber 11. A pump may be incorporated in conduit 4 to remove such fluids and to further lower the pressure on the aqueous side of the membrane. A plurality of appropriately-valved conduits 13 and 14 are employed to separately remove the aqueous and oil phases which readily form in separation chamber 11. The aqueous phase may be recycled from the separation chamber to conduit 5, if desired. In the case of hydrolizing oils such as melted tallow, the reaction products in chamber 11 will be fatty acids (oil phase) and glycerol (aqueous phase).

In the case of oil and aqueous reactants, when the oil phase is being pumped through the membrane, the membrane preferably is hydrophilic. Alternatively, if the aqueous phase is to be pumped therethrough, the membrane preferably is hydrophobic.

Conventional microporous or ultrafiltration membranes, supported or unsupported, may be employed in the practice of the present invention, including microporous acrylic, polypropylene, polysulfone, or cellulose nitrate membranes having pore diameters of 0.2 to 3 microns, and including ultrafiltration membranes wherein the largest molecule which will pass therethrough has a molecular weight of 2000 to 300,000.

A pressure differential across the membrane of about 1 to 50 psi is preferred. The higher pressures increase production rates and tend to increase reactivity, although, at the higher end of the spectrum, the catalyst life is reduced probably by the loss of some catalyst, which then requires more periodic replenishing of the catalyst. The upper pressure limit is restricted by the strength of the microporous membrane. Many of the membranes presently commercially available are able to withstand pressure differentials as high as 50 psi.

The membranes may be configured in a number of different ways including flat, pleated, spiral wound, tubular, or hollow fiber membranes.

The following is a description of a laboratory test of the present invention wherein a lipase enzyme-impregnated microporous membrane was employed to hydrolyze melted tallow oil.

Figure 3:
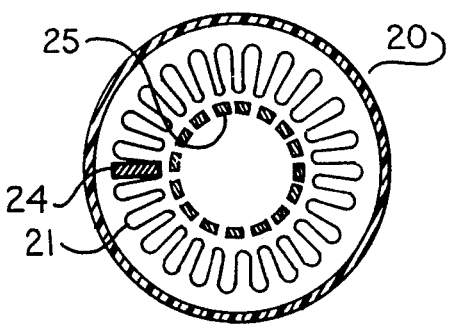
FIGS. 2-4 show reactor and membrane structure that can be used in the system of FIG. 1.
Figure 4:
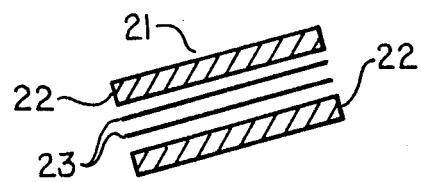
Figure 2:
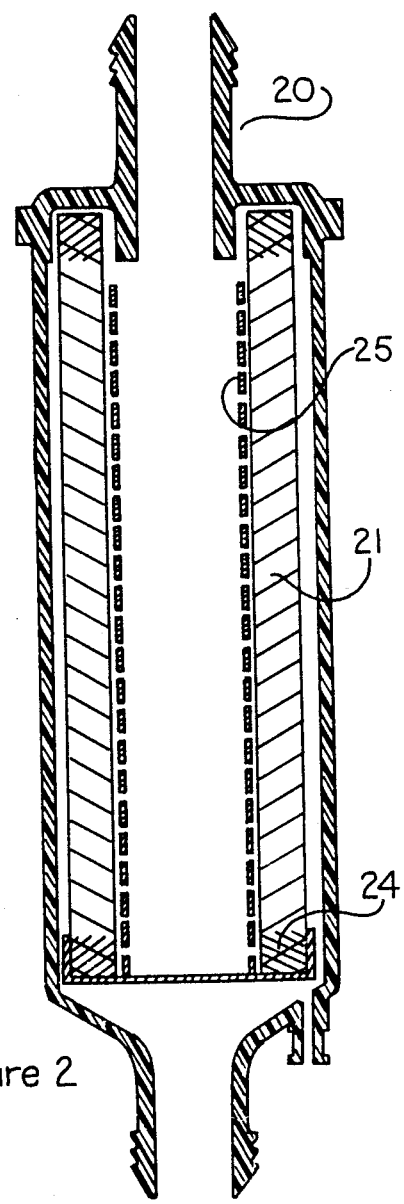

As shown in FIGS. 2-4, the apparatus for the test consisted of a commercially available reactor 20 having a membrane element 21 therein. The element consisted of a nonwoven support layer 22 having a thickness of about 0.25 mm, and a microporous membrane 23 (actually two membranes) sandwiched between layers 22. Each membrane 23 consisted of acrylic cast on nylon fabric, 0.2 micron pore diameter, thickness about 0.1 mm. The element 21 was pleated, 57 actual pleats. Polyurethane glue 24 was used to hold the two free ends of the pleats together, and to anchor the element in reactor 20.

A perforated support tube 25 helped to support the element 21. The shell of reactor 20 was composed of polycarbonate, and was 15.5 cm in length.

In the test, crude fermentation filtrate, 380 mL, containing 59,000 IU of lipase activity was drained through the reactor by gravity feed at pH 8. 68% of the lipase was retained or absorbed by the membrane. After the last of the enzyme solution had drained from the reactor, melted tallow at 45°-50° C. was poured in and the reactor was operated generally as shown in FIG. 1, with the entire apparatus maintained at 50° C. The initial flow rates were 0.09 g/min tallow, 0.12 mL/min buffer feed, 40 mM sodium acetate, pH 5.5 with 0.02% sodium azide, and 2.5 mL/min buffer recycle. The initial concentration of fatty acid in the tallow leaving the reactor was 1500 micromoles/g, or 42% by weight if the average molecular weight of fatty acid is estimated to be 282.

The initial activity of the reactor, calculated from the difference between the concentrations of fatty acid at the inlet and outlet of the reactor multiplied by the flow rate of tallow, was 130 micromoles/min. While the reactor was operated continuously for 140 days, the activity slowly decreased with a catalyst half-life greater than one month. The glycerol in the buffer leaving the reactor decreased gradually from an initial concentration of about 5 g/L. The pressure drop across the membrane was about 0.7 psi. While it was expected that the pressure drop would gradually increase over the almost six month test period, the pressure drop remained substantially constant throughout the period.

I claim:

1. A method of reacting a liquid oil with an immiscible aqueous liquid by means of a catalyst-impregnated membrane disposed between said oil and aqueous liquid comprising
    (a) impregnating a hydrophilic, microporous membrane with an enzyme catalyst to form said catalyst-impregnated membrane, said impregnating step consisting essentially of
        (i) passing an aqueous solution of said catalyst in contact with said hydrophilic, microporous membrane so that said catalyst is adsorbed by said membrane;
        (ii) removing said solution after said catalyst has been absorbed by said membrane;
    (b) thereafter passing said oil in contact with one side of said membrane, and passing said aqueous liquid in contact with the other side thereof;
    (c) creating a pressure drop across said membrane to force said oil to flow through said membrane to intermingle with said aqueous liquid on said other side of said membrane, thereby forming a coarse mixture with said aqueous liquid; and
    (d) separating said coarse mixture into two immiscible phases.

2. The method of claim 1 wherein said pressure drop is about 1-50 psi.

3. The method of claim 1 wherein said enzyme is lipase.

4. The method of claim 3 wherein said pressure drop is about 1-50 psi.

5. The method of claim 4 wherein said oil is melted tallow, wherein glycerol and fatty acids are produced by said reaction between said two fluids, wherein said fatty acids and glycerol separate from one another in said separation step.

* * * * *